(12) United States Patent
Thienphrapa et al.

(10) Patent No.: US 11,224,405 B2
(45) Date of Patent: Jan. 18, 2022

(54) MEDICAL NAVIGATION SYSTEM EMPLOYING OPTICAL POSITION SENSING AND METHOD OF OPERATION THEREOF

(71) Applicant: KONINKLIJKE PHILIPS N.V., Eindhoven (NL)

(72) Inventors: Paul Thienphrapa, Cambridge, MA (US); Bharat Ramachandran, Morganville, NJ (US); Molly Lara Flexman, Melrose, MA (US); Neriman Nicoletta Kahya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 260 days.

(21) Appl. No.: 16/305,917

(22) PCT Filed: Jun. 28, 2017

(86) PCT No.: PCT/EP2017/065946
§ 371 (c)(1),
(2) Date: Nov. 30, 2018

(87) PCT Pub. No.: WO2018/002109
PCT Pub. Date: Jan. 4, 2018

(65) Prior Publication Data
US 2020/0323514 A1 Oct. 15, 2020

Related U.S. Application Data

(60) Provisional application No. 62/356,566, filed on Jun. 30, 2016.

(51) Int. Cl.
*A61B 8/00* (2006.01)
*A61B 34/20* (2016.01)
(Continued)

(52) U.S. Cl.
CPC ......... *A61B 8/4254* (2013.01); *A61B 8/12* (2013.01); *A61B 8/463* (2013.01); *A61B 34/20* (2016.02);
(Continued)

(58) Field of Classification Search
CPC .. A61B 2017/00243; A61B 2034/2051; A61B 2034/2061; A61B 2034/254;
(Continued)

(56) References Cited

U.S. PATENT DOCUMENTS

2003/0212327 A1* 11/2003 Wang ............... A61B 6/502
600/437
2011/0113852 A1 5/2011 Prisco
(Continued)

FOREIGN PATENT DOCUMENTS

DE 10118570 A1 7/2002
WO 2014053934 A1 4/2014

*Primary Examiner* — Joanne M Hoffman
*Assistant Examiner* — Alexei Bykhovski

(57) ABSTRACT

An apparatus and method that uses shape sensing and imaging to record, display and enable return to an imaging probe location or to predetermined imaging parameters. The apparatus includes an ultrasound probe (104, 304, 404, 750); a shape-sensing-device (SSD) (102, 302, 602, 740) associated with the ultrasound probe; and a controller (122, 710). The controller may be configured to: determine at least one of location and orientation of the ultrasound probe based upon position sensor information (PSI) received from the SSD; select a view of a plurality of views of a workflow that are stored in the memory; obtain view setting information (VSI) including parameters and a position and/or orientation of the ultrasound probe for each of the views; determine guidance information; and render the determined guidance
(Continued)

information on the rendering device and set ultrasound probe parameters based on the parameters of the VSI for the selected view.

26 Claims, 7 Drawing Sheets

(51) Int. Cl.
*A61B 8/12* (2006.01)
*G16H 20/40* (2018.01)
*G16H 30/40* (2018.01)
*A61B 34/30* (2016.01)

(52) U.S. Cl.
CPC ............. *G16H 20/40* (2018.01); *G16H 30/40* (2018.01); *A61B 8/565* (2013.01); *A61B 2034/2051* (2016.02); *A61B 2034/2061* (2016.02); *A61B 2034/301* (2016.02)

(58) Field of Classification Search
CPC ........ A61B 2034/256; A61B 2034/301; A61B 2090/0818; A61B 2090/364; A61B 2090/365; A61B 2090/378; A61B 2090/3966; A61B 34/20; A61B 34/25; A61B 8/12; A61B 8/4254; A61B 8/4263; A61B 8/463; A61B 8/5223; A61B 8/565; G16H 20/40; G16H 30/40; G16H 50/30
See application file for complete search history.

(56) References Cited

U.S. PATENT DOCUMENTS

| | | |
|---|---|---|
| 2012/0245458 A1 | 9/2012 | Gogin et al. |
| 2013/0131499 A1 | 5/2013 | Chan et al. |
| 2013/0317356 A1 | 11/2013 | Ramachandran et al. |
| 2014/0121489 A1 | 5/2014 | Kommu |
| 2016/0171714 A1 | 6/2016 | Ekin et al. |
| 2016/0206381 A1 | 7/2016 | Grass et al. |
| 2017/0105701 A1* | 4/2017 | Pelissier ................ G16H 50/20 |
| 2017/0128145 A1 | 5/2017 | Hasser et al. |
| 2017/0265946 A1 | 9/2017 | Ramachandran et al. |

* cited by examiner

MEDICAL NAVIGATION SYSTEM EMPLOYING OPTICAL POSITION SENSING AND METHOD OF OPERATION THEREOF

CROSS-REFERENCE TO PRIOR APPLICATIONS

This application is the U.S. National Phase application under 35 U.S.C. § 371 of International Application Serial No. PCT/EP2017/065946, filed on Jun. 28, 2017, which claims the benefit of U.S. Patent Application No. 62/356,566, filed on Jun. 30, 2016. This application is hereby incorporated by reference herein.

FIELD

The present system relates to a medical navigation system which employs shape-sensing methods such as optical-shape-sensing (OSS) methods to perform tracking of a surgical implement during surgical interventions and, more particularly, to a medical navigation system which employs Fiber Optic RealShape™ (FORS) tracking methods to track surgical implements during surgical interventions, and methods of operation thereof.

BACKGROUND

Finding an optimal position and view to image an anatomy of an object such as a patient using ultrasound can be challenging especially during procedures such as surgical interventions. For example, during procedures such as structural heart disease procedures, a transesophageal echo (TEE) probe, which is a type of an ultrasound probe, may be placed such that a specific view of a heart of a patient may be obtained. However, more than one view from the TEE probe may be desired which may require a clinician to manipulate the TEE probe to other desired positions and/or orientations for these views and adjust ultrasound parameters for each of these views. Unfortunately, manipulating the position and/or orientation of the TEE probe and varying of the ultrasound parameters can take valuable time especially during surgical interventions. Further, in addition to wasting time, it is often difficult, if not impossible, to return to a previous view during a procedure. Thus, even the best ultrasound clinicians can find it challenging to work with TEE probes during surgical interventions.

EP2289452A2 of Christopher Hasser et al., published Jun. 5, 2006, entitled "Laparoscopic Ultrasound Robotic Surgical System" is directed to a laparoscopic ultrasound robotic surgical system comprising a first robotic arm mechanically coupled to an ultrasound probe; a second robotic arm mechanically coupled to a surgery related device; a master manipulator; a control switch having user selectable first and second modes; and a processor configured to cause the second robotic arm to be locked in position and the first robotic arm to move the ultrasound probe according to user manipulation of the master manipulator when the control switch is in the first mode, and cause the second robotic arm to manipulate a tool according to manipulation of the master manipulator and the first robotic arm to move the ultrasound probe according to stored instructions upon detection of a user command associated with the stored instructions when the control switch is in the second mode.

WO2015092581A1 of Bharat Ramachandran et al., published Jun. 25, 2015, entitled "Shape Sensed Robotic Ultrasound for Minimally Invasive Interventions" is directed to systems and methods for shape sensed robotic ultrasound for minimally invasive interventions. One or more medical devices, such as, e.g., an ultrasound probe and endoscope, are integrated with optical shape sensing. Shape sensing may be integrated with the one or more medical devices by securing at least one fiber to the one or more medical devices using, e.g., a sleeve, shrink tubing, a channel within the probe, patch attachment, etc. Based on the shape sensing data, a registration is performed between the one or more medical devices. Registration may be, e.g., landmark-based, fixture-based, image-based, etc. In some embodiments, the one or more medical devices are coupled to one or more moveable features of a configurable device or robot for robotic guidance. The one or more moveable feature may also be integrated with shape sensing such that their relative positions are known.

US20140121489 A1 of Mohan Krishna Kommu CHS, published May 1, 2014, entitled "Medical Imaging System and a Portable Medical Imaging Device for Performing Imaging" is directed to a portable medical imaging device for performing imaging procedures. The portable medical imaging device comprises a processor configured to analyze location information associated with the portable medical imaging device. Then it is determined whether the location information is linked to a location of performing an imaging procedure. The processor selects an imaging configuration from a plurality of imaging configurations associated with an imaging procedure to be performed in the location. Each imaging configuration of the plurality of imaging configurations is associated with a type of imaging procedure. The plurality of imaging procedures is stored in at least one memory communicably coupled to the processor. The selected imaging configuration is loaded to perform the imaging procedure.

Accordingly, embodiments of the present system may overcome these and other disadvantages of conventional imaging systems.

SUMMARY

The system(s), device(s), method(s), arrangements(s), user interface(s), computer program(s), processes, etc. (hereinafter each of which will be referred to as system, unless the context indicates otherwise), described herein address problems in prior art systems. Embodiments of the present system may employ shape sensing registration methods which may employ sample points, such as what may be considered a discrete set or a continuum of simultaneous sample points which may provide information related to a position of a coordinate system so that disparate coordinate systems may be registered.

In accordance with embodiments of the present system, there is disclosed, in one aspect of the present system, a surgical guidance system including a memory; a rendering device; an ultrasound probe; a shape-sensing-device (SSD) associated with the ultrasound probe and having a predetermined position and orientation with regard to the ultrasound probe, a controller coupled to the memory, the rendering device and the SSD, the controller configured to: determine at least one of location and orientation of the ultrasound probe based upon position sensor information (PSI) received from the SSD; select a view of a plurality of views of a workflow that are stored in the memory; obtain view setting information (VSI) for the selected view from the memory, the VSI comprising parameters and at least one of a position and orientation of the ultrasound probe for each of the views; determine guidance information based upon a comparison of the determined location and orientation of the ultrasound probe and the at least one of a position and orientation of the ultrasound probe for the selected view; and render the determined guidance information on the rendering device and set ultrasound probe parameters based on the parameters of the VSI for the selected view.

In accordance with embodiments of the present system, the SSD may include at least one position sensor and the controller may be configured to query the at least one position sensor to obtain the PSI, the PSI being indicative of at least one of a position and orientation of the at least one position sensor relative to a workspace. It is further envisioned that the controller may be further configured to render the determined guidance information as directional indications to guide the ultrasound probe to at least one of a position and orientation of the ultrasound probe for the selected view. The controller may be further configured to display simultaneously on the rendering device two or more of the plurality of views of the workflow. The controller may be further configured to display on the rendering device an indication for each of the two or more views. It is also envisioned that the controller may be further configured to display on the rendering device the two or more views as a single view with the two or more views anatomically positioned.

In accordance with embodiments of the present system, the controller may be coupled to at least one transducer of the ultrasound probe to obtain ultrasound image information using the set ultrasound probe parameters. It is further envisioned that the controller may be further configured to reconstruct an image based upon the ultrasound image information in accordance with the set ultrasound probe parameters. The controller may be further configured to associate and store two or more of current parameters, location, orientation, and ultrasound information of the ultrasound probe in association with the selected view. It is also envisioned that the controller may be further configured to determine which of the plurality of views is closest to the determined at least one of location and orientation of the ultrasound probe and select the view based on which view is determined closest.

In accordance with embodiments of the present system, there is further disclosed a method for guiding an ultrasound probe for obtaining ultrasound information performed by at least one controller and comprising acts of: determining at least one of location and orientation of the ultrasound probe based upon position sensor information (PSI); selecting a view of a plurality of views of a workflow that are stored in a memory; obtaining view setting information (VSI) for the selected view, the VSI comprising information related to parameters and at least one of a position and orientation of the ultrasound probe for each of the views; determining guidance information based upon a comparison of the location and orientation of the ultrasound probe and the at least one of a position and orientation of the ultrasound probe for the selected view; and outputting the determined guidance information and setting ultrasound probe parameters based on the parameters of the VSI for the selected view. The method may further include an act of querying at least one position sensor of a shape-sensing-device (SSD) to obtain the PSI, the PSI being indicative of at least one of a position and orientation of the at least one position sensor relative to a workspace.

It is further envisioned that the act of outputting of the determined guidance information includes acts of generating guidance instructions corresponding to the determined guidance information and rendering the generated guidance instructions on a rendering device of the system. The act of outputting of the determined guidance information may include an act of transmitting the guidance information to at least one robotic actuator to control at least one of position and orientation of the ultrasound probe. It is also envisioned that the act of outputting includes an act of outputting the determined guidance information as directional indications to guide the ultrasound probe to at least one of a position and orientation of the ultrasound probe for the selected view. It is further envisioned that the method may include an act of displaying simultaneously on the rendering device two or more of the plurality of views of the workflow.

In another aspect of the present system a user interface presents guidance instructions and guidance information which may correspond to determined VSI or probe parameters or choice of workflows.

In accordance with embodiments of the present system, there is further disclosed a non-transitory computer readable medium that comprises computer instructions which, when executed by a processor, configure the processor to perform acts of: determining at least one of location and orientation of an ultrasound probe based upon position sensor information (PSI); selecting a view of at least one registered view of a workflow; obtaining view setting information (VSI) for the selected view, the VSI comprising information related to parameters for each of the registered views and at least one of a position and orientation of the ultrasound probe for each of the views; determining guidance information based upon a comparison of the location and orientation of the ultrasound probe and the at least one of a position and orientation of the ultrasound probe for the selected view; and outputting the determined guidance information and setting ultrasound probe parameters based on the parameters of the VSI for the selected view. It is also envisioned that the instructions may configure the processor to perform an act of querying at least one position sensor of a shape-sensing-device (SSD) to obtain the PSI, the PSI being indicative of at least one of a position and orientation of the at least one position sensor relative to a workspace. It is further envisioned that the instructions may configure the processor to perform an act of displaying simultaneously two or more of the plurality of views of the workflow. The processor may further be configured by the instructions to perform the act of displaying simultaneously the two or more of the plurality of views as a single view with the two or more views anatomically positioned.

BRIEF DESCRIPTION OF THE DRAWINGS

The present system is explained in further detail in the following exemplary embodiments and with reference to the figures, where identical or similar elements are partly indicated by the same or similar reference numerals, and the features of various exemplary embodiments being combinable. In the drawings.

DETAILED DESCRIPTION

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques, and methods are omitted so as not to obscure the description of the present system. It should be expressly understood that the drawings are included for illustrative purposes and do not represent the entire scope of the present system. In the accompanying drawings, like reference numbers in different drawings may designate similar elements. The term and/or and formatives thereof should be understood to mean that only one or more of the recited elements may need to be suitably present (e.g., only one recited element is present, two of the recited elements may be present, etc., up to all of the recited elements may be present) in a system in accordance with the claims recitation and in accordance with one or more embodiments of the present system.

For the sake of clarity, embodiments of the present system will be shown and described with respect to shape sensing devices (SSDs) such as shape-sensing fibers as may be employed using FORS methods and the like. However, it is also envisioned that embodiments of the present system may be compatible with other tracking systems which may sample multiple data points sequentially or simultaneously such as EM tracking methods and the like. Further, it should be assumed that SSDs of the present system may be used alone or with a sheath such as a catheter, a guidewire, a surgical tool, an imaging tool (e.g., an ultrasound probe), and the like.

Figure 1:
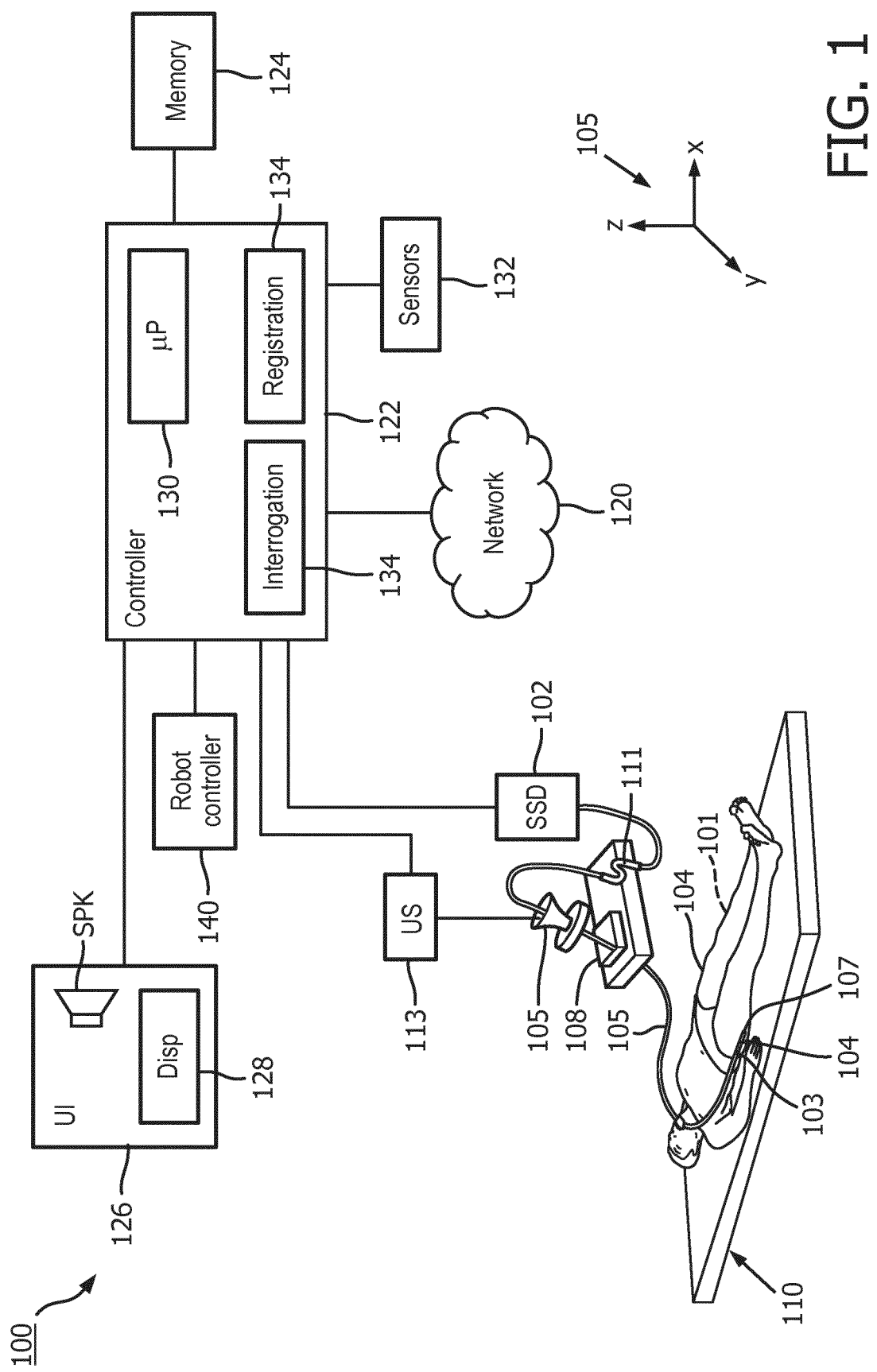
FIG. 1 shows a perspective front view of a portion of an ultrasound medical navigation system operating in accordance with embodiments of the present system.

FIG. 1 shows a perspective front view of a portion of an ultrasound medical navigation system 100 (hereinafter system 100 for the sake of clarity) operating in accordance with embodiments of the present system. The system 100 may include one or more of an SSD 102, an ultrasound probe 104, a base 108, a support platform 110, a controller 122, a robotic controller 140, a network 120, a memory 124, sensors 132, and a user interface (UI) 126. The controller 122 may control the overall operation of the system 100 and may communicate with one or more of the SSD 102, the ultrasound probe 104, the base 108, the support platform 110, the memory 124, the sensors 132, the robotic controller 140, and the UI 126 using any suitable wired and/or wireless communication methods. For example, the controller 122 may communicate with the ultrasound probe 104 via the network 120. The robotic controller 140 may be operative to robotically manipulate one or more surgical implements of the present system such as the ultrasound probe 104 to a desired position and/or orientation. Accordingly, the robotic controller 140 may include one or more actuators, arms, etc. to manipulate the ultrasound probe 104 along or about one or more axes (e.g., multiple axes such as 7, etc.).

The network 120 may include any suitable communication link such as a wide-area network (WAN), a local-area network (LAN), the Internet, a system bus, a proprietary bus, the Internet, an intranet, a wired bus, a wireless bus, etc. Accordingly, a user may communicate with the system using local and/or remote communication methods. The memory 124 may include any suitable non-volatile memory in which information such as operating instructions, information generated by the system, user inputs and/or settings, historical information, operating settings and/or parameters, identification information, user information, patient information, etc., may be stored.

The sensors 132 may include sensors which may obtain corresponding sensor information and provide this sensor information to the controller 122 for further processing. The controller 122 may query one or more of the sensors 132 for the sensor information. For example, the sensors 132 may include optical-shape-sensors which may sense a shape of the SSD 102 and provide this information to the controller 122 which may determine position and/or orientation of one or more portions of the SSD 102 in accordance with embodiments of the present system. The sensors 132 may be distributed throughout the system 100 and may further include sensors such as touch sensors, a keyboard, etc., with which a user may enter information into the system. The sensors 132 may further include an EM tracking sensor. Further, the sensors 132 may include position sensors which may provide position/orientation information related to a position/orientation of the support platform 110, the patient 101, the base 108, an EM tracker, etc.

The UI 126 may include any suitable user interface which may render information for the convenience of user such as graphical user interfaces (GUIs) generated by the system and/or image information. Accordingly, the UI 126 may include a speaker (SPK), a display 128 (e.g., a touch-screen display, etc.), haptic device (e.g., vibrators, etc.). The support platform 110 may be any suitable support platform which may support an object such as a patient 101 in a desired position and/or orientation for a procedure such as an interventional procedure. The support platform 110 may include actuators which may move the support platform under the control of the controller 122.

The base 108 may include any suitable device base or bases (physical or virtual) which may function as a launch fixture for one or more of the ultrasound probe 104 and the SSD 102. Accordingly, a position and/or orientation at least a portion of one or more of the ultrasound probe 104 and the SSD 102 may be determined relative to a reference frame. The base 108 may include a plurality of bases. The reference frame may include any suitable reference frames such as a reference frame of the support platform 110, a reference frame of the patient 101, a common reference frame, etc. However, for the sake of clarity, it will be assumed that the reference frame may refer to the reference frame of the patient 101. Thus, the reference frame may correspond with the anatomy of the patient 101. Accordingly, the system 100 may employ a workspace as defined by the patient 101 for the sake of clarity. This workspace may be referred to as the patient workspace. The base 108 may be coupled to any suitable fixture such as a C arm, the support platform 110, etc.

The ultrasound probe 104 may include any suitable ultrasound probe for a procedure being performed. For example, in the present embodiments the ultrasound probe 104 may be assumed to include a transesophageal echo (TEE) probe which may obtain ultrasound image information for constructing images of the heart of the patient 101 for one or more views (e.g., viewpoints). Further, it will be assumed that for each view, position, orientation, settings and/or parameters of the ultrasound probe 104 may be varied. The ultrasound probe 104 may include an ultrasound sensor (e.g., transducer) array 106 for capturing, the ultrasound image information for each view. The ultrasound sensor array 106 may be situated at, or adjacent to, a distal end 107 of the ultrasound probe 104. The ultrasound probe 104 may include an opening suitable for receiving the SSD 102 so that a position and/or orientation of, for example, a portion of the ultrasound probe 104 such as the ultrasound sensor array 106 may be easily determined. However, and without limitation, it should be understood that the opening may include a notch or tab suitable for receiving a portion of the SSD 102 as may be desired. This notch or tab may be located at a desired position on the ultrasound probe 104 such as at or near the distal end 107 of the ultrasound probe 104. The opening may be configured to receive the SSD 102 such that the position and orientation of the SSD 102 relative to the opening may be defined. For example, the opening may be keyed to receive the SSD 102 only in a single position such that position and/or orientation of the SSD 102 may be determined relative to the ultrasound probe 104. The position and/or orientation may be determined using a position and/or orientation vector. However, in yet other embodiments, the ultrasound probe 104 may be set at a known distance from the SSD 102 (e.g., see, FIGS. 3-6).

The ultrasound probe 104 may be located at a distal end of a sheath 105. The sheath 105 may include one or more openings along a length thereof through which the SSD 102 may be inserted to reach the ultrasound probe 104. Similarly, the ultrasound probe 104 may be inserted through the same or another opening. Accordingly, the ultrasound probe 104 and the SSD 102 may be simultaneously located within the sheath 105. However, in accordance with yet other embodiments, the ultrasound probe 104 and the SSD 102 may be inserted through different lumens.

The ultrasound probe 104 may communicate with the controller 122 using any suitable wired and/or wireless communication method. For example, the ultrasound probe 104 may communicate with the controller 122 via the network 120. The controller 122 may control the ultrasound sensor array 106 to generate ultrasound information suitable for generating an ultrasound image of a desired view (e.g., a desired viewpoint). The ultrasound probe 104 may include identifying landmarks which may be recognized in one or more images of the system such as x-ray images and a corresponding position and/or orientation of the ultrasound probe 104 may be determined. Thereafter, a registration may be performed to register images obtained from the ultrasound probe 104 to the x-ray images, etc. and a position and/or orientation of the ultrasound probe 104 may be determined based upon the x-ray images of the ultrasound probe 104. Suitable registration methods may be discussed in U.S. Patent Publication No. 2012/0245458 which shows registration between X-ray and ultrasound and International Patent Publication Nos. WO 2014/053934A1 which shows registration between FORS and ultrasound WO2015010859 which shows registration between FORS and X-ray, the contents of each of which are incorporated herein by reference. As readily appreciated, other suitable image registration methods may also be suitably applied for registering portions of the present system.

The SSD 102 may include at least one sensor which may provide SSD information suitable for determining a position and/or orientation of at least a portion of the SSD 102 relative to a desired reference frame such as a reference frame of the patient 101 (e.g., the patient workspace). For the sake of clarity, it may be assumed that the SSD 102 may pass through at least a portion of the opening of the ultrasound probe 104 such that a distal end 103 of the SSD 102 may be situated at the ultrasound probe 104. For example, the SSD 102 may be coupled to the ultrasound probe. However, in yet other embodiments, the SSD 102 may be situated a known distance from the ultrasound probe 104, if desired, and a known offset distance and/or orientation may be used to determine the position and/or orientation of the ultrasound probe 104. The SSD 102 may further pass through or within a known path such as a known path 111 (which may be coupled at a known position and/or orientation to, for example, the base 108) which may be recognized by the system 100 for registration. The ultrasound probe 104 may include a known path, for example so that when situated within this known path, this known path may be recognized (e.g., through an analysis of SSD information), and a position and/or orientation of ultrasound probe 104 or portions thereof such as portions at or adjacent to this known shape, may be determined.

Referring back to the controller 122, the controller 122 may control the overall operation of the system 100 and may include one or more logic devices such as processors 130 (e.g., microprocessors (μP), etc.) having multiple interconnected semiconductor devices such as transistors, gates, impedance devices, metallization connections and the like, discrete and/or distributed logic gates and switching devices, and/or the like. The controller 122 may include an interrogation module 134 and/or a registration module 136 which may include hardware, software and/or firmware devices with instructions stored in a memory thereof and/or the memory 124, which when executed by the processor cause the processor to perform one or more desired functions.

The interrogation module 134 may be operative to obtain information from the SSD 102 (e.g., via an interrogation process) such as SSD information (SSDI) (which will be described below) and which may indicate a path travelled by the SSD 102 over time and/or a shape of one or more portions of the SSD 102. The path may be determined serially (e.g., over time) and/or simultaneously (e.g., at a single time). The SSDI may then be processed to determine a location and/or orientation of the ultrasound probe 104. When placed through or within a known path or one or more known paths (e.g., 111), The SSD may assume a shape of the corresponding known more known paths and form corresponding SSDI. The controller 122 may recognize this known path (e.g., through an analysis of the SSDI) and determine a position and/or orientation of one or more portions of the SSD 102 relative to the correspondingly recognized known path. However, it is also envisioned that a position and/or orientation of a known path (e.g., a known path in the ultrasound probe 104) may be determined based upon the SSDI.

The registration module 136 may be operative to register the position and/or orientation of the SSD 102 and/or the ultrasound probe 104 relative to one or more reference coordinate systems such a workspace of the patient 101 (e.g., the patient workspace which may reflect an anatomy of the patient 101) as used in the current embodiments. For example, the registration module 136 may register one or more portions of the system (and/or information obtained therefrom) such as an EM tracking system (e.g., an EM generator and/or an EM sensor), an x-ray imager, the SSD, and the ultrasound probe 104 for example to a workspace of the patient 101. The registration module 136 may further register one or more portions of the system 100 such as the base 108, known shapes (e.g., the shape of known path 111), etc., as may be desired, to a known workspace such as the patient workspace. For example, it is envisioned that the registration module 136 may register images obtained from one or more imaging modalities of the system such as an X-ray images (e.g., which may be obtained in real time), ultrasound images (e.g., an ultrasound views), patient anatomy, a position of the SSD 102 (e.g., via SSD information), one or more workspaces, etc. For example, the X-ray images may be registered to an ultrasound view, and/or an SSD, which may ultimately be registered to a workspace of the patient 101 (e.g., the patient anatomy for the sake of clarity) or vice versa. An order of registration may vary. The system 100 may include software to perform registration such as an echo navigator, etc.

The SSD 102 may extend from the base 108 for a given length ($L_{ssd}$) and may provide signals such as SSDI indicative of its position and/or orientation along at least a portion of its length ($L_{ssd}$). The SSDI may further include information related to a shape of the SSD 102 at one or more locations thereof, if desired. The SSD 102 may be formed using any suitable shape-sensing device such as a Fiber Optic RealShape™ (FORS) fiber or the like which may provide sensor information (e.g., SSDI) from a plurality of sensors indicative of position and/or orientation of a plurality of locations along its length $L_{ssd}$. Each of the sensors may provide information related to, for example, a position (e.g., an x, y, z coordinate, etc.) and/or orientation (e.g., twist of a corresponding fiber) of the corresponding sensor. The plurality of shape sensing locations may approach a continuum of locations, as desired. However, generally, the plurality of shape sensing locations may be set apart from each other by a desired distance such as 40 µm or other suitable distance. Suitable SSDs 102 may include, for example, a shape sensing fiber (SSF), an EM-based tracking device with at least one EM sensor such as an EM sensor located at a tip thereof, etc., and/or combinations thereof, such as described in U.S. Patent Publication No. 2013/0317356 to Ramachandran et al., which is incorporated herein by reference in its entirety. In accordance with embodiments of the present system, the position and/or orientation sensors may be active light emitting diodes, passive reflectors such as spheres, optical and/or EM coils, and/or radioactive or radiopaque markers which are identifiable based on imaging such as X-ray and/or nuclear based imaging. Similarly to the optical sensors, the EM sensors and/or other sensors/markers may be situated at one or more locations apart from each other as may be desired, or a shape may be reconstructed from a single point sensor by accumulating a history of positions as the SSD is passed through a path.

During operation, the SSDI may be obtained by interrogating the SSD 102. The interrogation may employ optical and/or EM interrogation techniques which may correspond with a type of the SSD employed by the system. For example, the SSF may employ Fiber Optic RealShape™ (FORS) interrogation techniques to determine position and/or orientation thereof, while the EM-based tracking device may employ EM interrogation methods to obtain the SSDI. However, it should be understood that these interrogation techniques may or may not be exclusive of each other. For example, two or more of these techniques may be utilized together. Further, the optical interrogation technique may interrogate at least one optical sensor of the SSD synchronously in time and the EM interrogation technique may interrogate at least one EM sensor of the SSD sequentially in time and/or vice versa.

Regardless of the type of interrogation technique, the interrogation may obtain the SSDI which may then be processed to perform a registration of the SSD 102 to a reference workspace coordinate system (e.g., the patient workspace) as described in this application and/or to determine a location and/or orientation of one or more portions of the SSD 102 such as a distal end 103 of the SSD 102. The controller 122 may be communicatively coupled (using any suitable method such as electronically, optically, etc.) to the SSD 102 so that the SSD 102 may be interrogated. For the sake of clarity, it is assumed that the workspace of the patient 101 may be referred to as a reference workspace. However, it should be understood that there may be several reference workspaces in a system operating in accordance with embodiments of the present system. In accordance with embodiments of the present system, the controller 122 may drive an EM field generator which may obtain EM field information from the SSD 102 when the employing an EM-type SSD.

Figure 2:
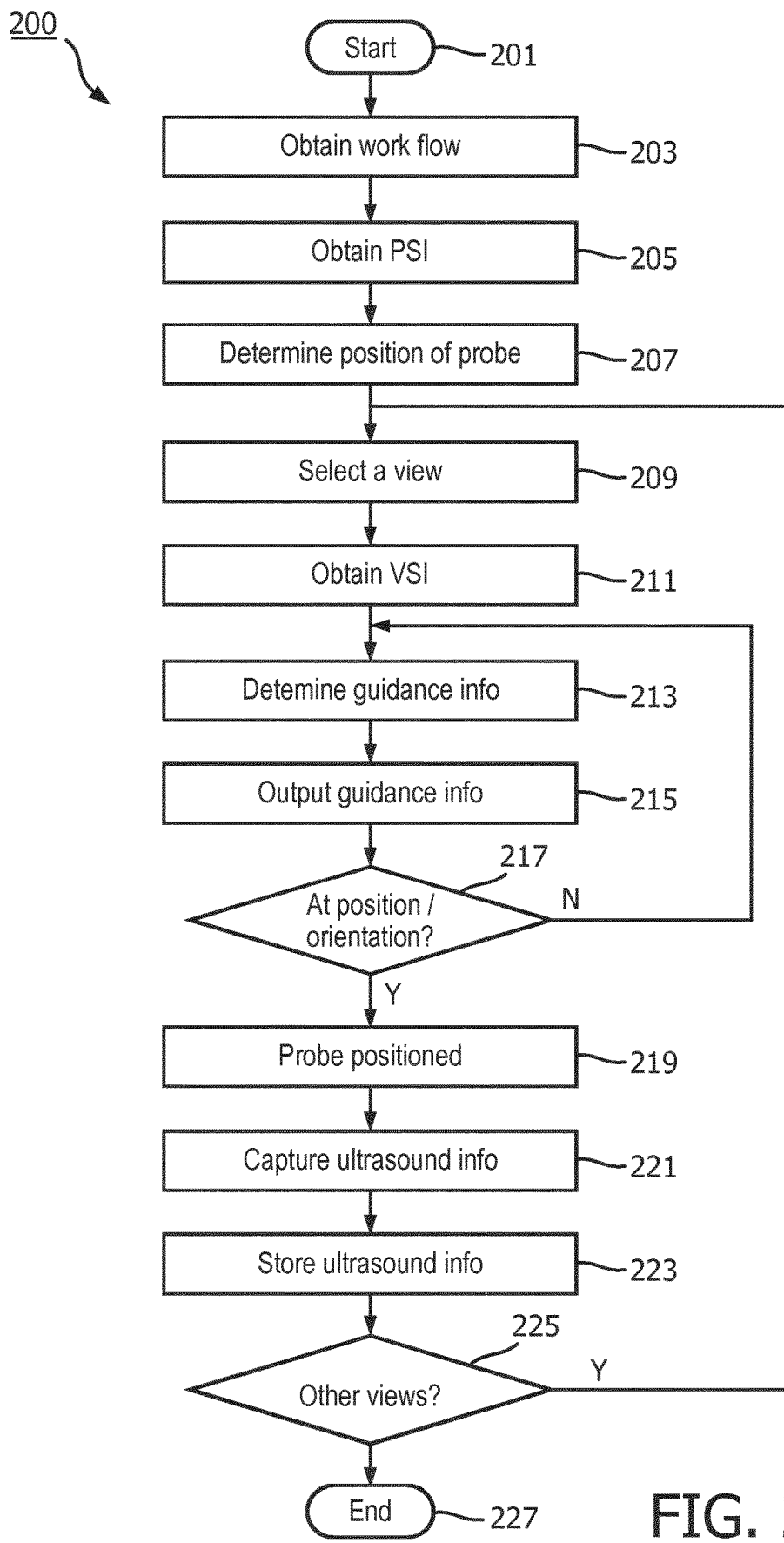
FIG. 2 shows a functional flow diagram performed by a process in accordance with embodiments of the present system.

FIG. 2 shows a functional flow diagram performed by a process 200 in accordance with embodiments of the present system. The process 200 may be performed using one or more processors, computers, controllers, etc., communicating over a network and may obtain information from, and/or store information to one or more memories which may be local and/or remote from each other. The process 200 may include one of more of the following acts. In accordance with embodiments of the present system, the acts of process 200 may be performed using one or more suitable coordinate registration systems operating in accordance with embodiments of the present system. Further, one or more of these acts may be combined and/or separated into sub-acts, as desired. Further, one or more of these acts may be skipped depending upon settings. For the sake of clarity, the process may be described with reference to a single ultrasound probe. However, without limitation, it should be understood that the process may employ a plurality of ultrasound probes each of which may be include a separate workflow such as a sub-workflow. In operation, the process may start during act 201 and then proceed to act 203. Further, it will be assumed that the ultrasound probe may include a known path.

Figure 3:
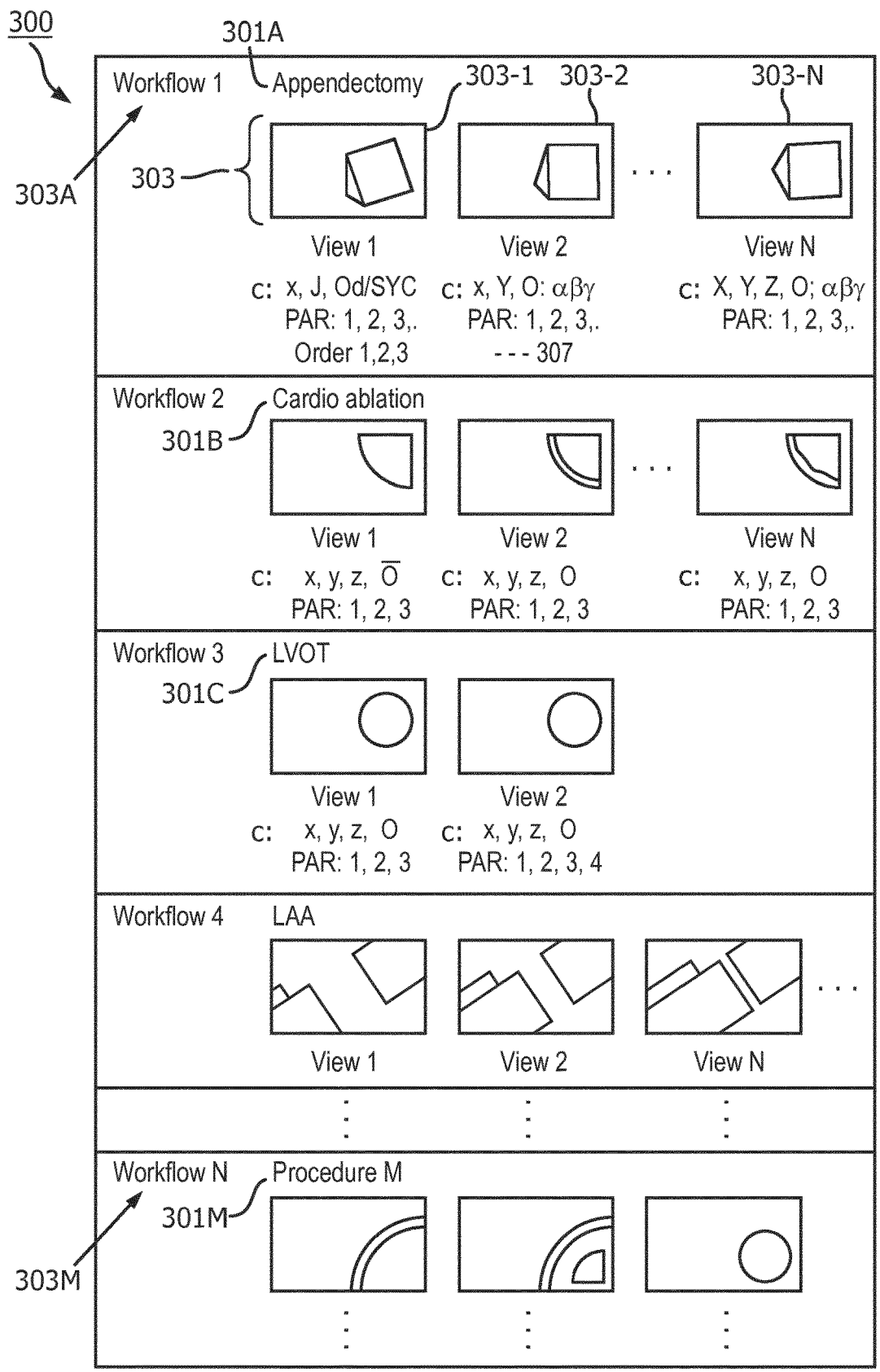
FIG. 3 shows a workflow table for each of a plurality of PTs in accordance with embodiments of the present system.

During act 203, the process may obtain a workflow for a current procedure. This workflow may be referred to as a current workflow. The workflow may be obtained from workflow information (WI) which may include information corresponding with a current procedure or workflow if known. The workflow may have associated with it a plurality of registered views (e.g., viewpoints) each of which may image information and corresponding location (e.g., x, y, z, etc.), orientation information (e.g., α, β, γ, etc.), and/or ultrasound parameter settings. In accordance with embodiments of the present system, these views may be stored as a view library for each workflow. The workflow may correspond with a procedure-type (PT) being performed and may be obtained from a memory of the system in accordance with the PT being performed and/or may be designated by a user. Thus, a workflow may be defined in accordance with a procedure-type (PT) and/or a user (performing the procedure). For example, in accordance with embodiments of the present system, a workflow for a PT may include one or more procedures (e.g., sub-procedures) which may be performed in any desired order as may be set by the system and/or the user. For example, FIG. 3 shows a workflow table 300 for each of a plurality of PTs 301$x$ in accordance with embodiments of the present system. With reference to FIG. 3, assuming that there are M procedure types 301A through 301M, wherein M is an integer (generally 301$x$), each procedure type (e.g., appendectomy, cardio ablation, etc.) may have a corresponding workflow 303A through 303M (e.g., workflow 1 through M, where M is an integer) associated therewith. Each workflow may have corresponding information associated therewith such as one or more of registered views (RVs) 303 and associated information such as coordinate information (CI), orientation information (OI), view order information 307 (e.g., including information related to suitable orders to obtain views as desired), and parameter information (e.g., for setting parameters of the ultrasound probe) for each registered view. For example, with reference to registered view 303-1, there may be corresponding view setting information (VSI) which may include information such as coordinate information (CI) (x, y, z), orientation information (OI) ($\alpha$, $\beta$, $\gamma$), and parameter information (Param). The parameter information may include information related to parameters and/or other settings for an ultrasound probe used by the present system to obtain ultrasound images. The workflow table 300 may be stored in a memory of the system and may be set/reset by the system and/or the user. For example, the system may render the workflow table 300 so that a user may select a PT and see a corresponding workflow. Further, each workflow may be registered to a workspace of the system. Further, each registered view may include one or more landmarks as may be desired.

It is further envisioned, that the plurality of registered views may be stored in a memory of the system and may be selected based upon a type of procedure being performed. For example, a procedure of type I may have a workflow which may include 5 views assigned to it, while a procedure of type II (different from type I) may have a workflow which may include 6 views assigned to it. For example, in accordance with embodiments of the present system a Left Ventricular Obstruction Track (LVOT) setting may include a workflow including predefined registered views for determining, for example, a left ventricular obstruction track. Other procedures may correspond with, for example, a transseptal puncture, a mitral valve navigation, deploying an LAA closure, etc. Thus, a type of procedure may be determined during an initial setup, for example automatically determined by a processor based on stored patient data and/or selected by a user, etc., and the view or views may be selected based upon the determined procedure. Further, the views may further be defined by a user and/or procedure type. Thus, user A may have different views stored than user B regardless of the procedure type. After completing act 203, the process may continue to act 205.

During act 205, the system may obtain position sensor information (PSI) which may be indicative of a position and/or orientation of at least a portion of the SSD such as a distal end of the SSD. The PSI may include SSD information (SSDI) which may be obtained by interrogating the SSD to obtain the SSDI from a plurality of shape-sensing sensors each at a corresponding location of the SSD which sensor information may be indicative of position and/or orientation of a plurality of corresponding locations along the length $L_{ssd}$ of the SSD. For example, the system may employ a FORS method to interrogate the SSD to obtain the SSDI. Further, the plurality of shape-sensing locations may approach a continuum of locations, as desired. Thus, during an interrogation, the system (e.g., a suitably programmed processor of the system) may interrogate the at least one sensor of the SSD sequentially and/or synchronously over time to obtain position information from at least one sensor and form corresponding SSDI. This SSDI may then be reconstructed by the processor to determine a path (P) of the SSD and to determine a position and/or orientation of at least a portion of the SSD such as a distal end of the SSD.

Suitable SSDs may include, for example, a shape sensing fiber (SSF), an EM-based tracking device with at least one EM sensor such as an EM sensor located at a tip thereof, etc., and/or combinations thereof, such as described in U.S. Patent Application Publication No. 2013/0317356 to Ramachandran et al. The position and/or orientation sensors may include active light emitting diodes, passive reflectors such as spheres, optical and/or EM coils, and/or radioactive or radiopaque markers which are identifiable based on imaging such as X-ray and/or nuclear based imaging. Similarly to the optical sensors, the EM sensors and/or other sensors/markers may be situated at one or more locations apart from each other as may be desired, or a shape may be reconstructed from a single point sensor by accumulating a history of positions as the SSD is passed through a known path. Accordingly, during this act an interrogation module (e.g., in a form of one or more hardware devices, software portion programming a portion of the processor and/or a dedicated processor) may be operative to obtain information from the SSD (e.g., via an interrogation process) such as the SSDI and which may indicate a path travelled by the SSD 102 over time and/or a shape of one or more portions of the SSD 102. After completing act 205, the system may continue to act 207.

During act 207, the system may determine at least one of position and orientation of the ultrasound probe (or a particular ultrasound probe if a plurality of ultrasound probes is desired) based upon the position sensor information (PSI). The PSI may be indicative of at least one of a position and orientation of the at least one position sensor of the SSD relative to the workspace. As the SSD may be positioned in a known relation (e.g., a known offset) to the ultrasound probe, the position and/or orientation of the ultrasound probe may be determined in accordance with the PSI and/or an SSD-to-ultrasound probe transformation for example assuming a known offset. This known offset may be previously determined and stored in a memory of the system for later use and/or the offset may be determined or confirmed during use.

For the sake of clarity, the workspace may be defined as a workspace of the system and may be a general workspace or may be workspace defined relative to an object being scanned such as a patient. Thus, for the sake of clarity, the workspace may be defined as a workspace of the patient and, thus, may correspond with an anatomy of a patient such as the patient and/or a common workspace (e.g., common to the devices of the present system). Further, it will be assumed that a registration process to register one or more of an X-ray imager, the SSD, and the ultrasound probe to a workspace of the system may have been performed and/or may be performed during use.

It is further envisioned that the system may employ image analysis (e.g., of a captured ultrasound image) to determine a location of the ultrasound probe relative to a known view such as a registered view which may be registered in a memory of the system. Accordingly, the system may obtain ultrasound information from the ultrasound probe and determine a corresponding position and/or orientation of the ultrasound probe based upon this ultrasound information using any suitable method such as using image analysis of the ultrasound information and thereby, form corresponding PSI relative to the known anatomy of the patient and, thus, the patient workspace. Thereafter, the process may update the PSI accordingly to include this information. For example, the ultrasound image information may include one or more landmarks which may correspond with known landmarks in a registered view(s) relative to the workspace. Accordingly, difference information between location and/or orientation of the known landmarks and corresponding information in the ultrasound image information may be determined and thereafter this difference information may be used to determine a position and/or orientation of the ultrasound probe relative to the workspace.

In addition, position information and/or orientation for interventional devices such as one or more additional ultrasound devices, catheters, ablative devices, etc., may be acquired for example using a SSD or other device/system for acquiring such information such as described herein. Further, one or more images may be acquired of the interventional devices which may be saved, recalled and rendered. For example, the one or more images of the interventional device(s) may be rendered in an image including the ultrasound instrument, a view of a workflow, etc., such as illustratively depicted in FIGS. 4A, 4B, 5 and 6. After completing act 207, the system may continue to act 209.

During act 209, the system may select a registered view (hereinafter the selected view) from a plurality of registered views of the current workflow using any suitable method. For example, in accordance with embodiments of the present system, the selected view may be selected from the plurality of registered views based upon the view order information (e.g. view order 1, 3, 4, 5, 7, etc.), a user selection (e.g., select registered view 3, etc., which may be selected using a user input device of the system such as a touch-screen, a keyboard, a microphone, etc.). However, it is also envisioned that the order of the plurality of registered views, may be selected from a default selection. Thus, if there are five consecutive registered views previously defined for the current workflow, the system may obtain these registered views in any suitable order (e.g., first to last, vice versa, randomly selected, based upon location of the ultrasound probe (nearest to furthest), etc.) as may be set by the system and/or user.

In accordance with embodiments of the present system, the selected view may be selected based upon the determined location and orientation of an ultrasound probe. For example, if is it determined that the determined position of the ultrasound probe is within a threshold distance $\Delta_{DIS}$ of a registered view (e.g., a view of the views), the system may set this view as a selected view. Similarly, in a case where it is determined that the determined orientation of the ultrasound probe is within a threshold orientation $\Delta_{ORIENT}$ of a view (e.g., a given view of the views), the system may set this view as a selected view.

In accordance with embodiments of the present system, it is envisioned that the system may select a view from the plurality of views when both the determined position of the ultrasound probe is within a threshold distance $\Delta_{DIS}$ of a view and the determined orientation of the ultrasound probe is within a threshold orientation $\Delta_{ORIENT}$ of the view. The system may define the position and/or orientation of the ultrasound probe using a vector or the like. In accordance with embodiments of the present system each view may have defined thresholds such as a threshold orientation $\Delta_{ORIENT}$ (e.g., defined orientation +/−$\Delta_{ORIENT}$) and a threshold distance $\Delta_{DIST}$ (e.g., defined position +/−$\Delta_{DIST}$) defined.

In accordance with other embodiments, the view may be selected by a user such as a clinician performing an ultrasound-based imaging procedure. Accordingly, the process may provide one or more keys (e.g., hard, soft, etc.), menu items, etc., that the user may choose to select (e.g., by toggling, etc.) a registered view of a plurality of registered views. For example, the system may render one or more menu items (e.g., circles) on an image which may represent a view. The user may then select any of these menu items to select the corresponding registered view and the system may set this view as a selected view. These menu items may be superimposed upon an image of a region-of-interest (ROI). Thus, with reference to FIG. 3, the process may render registered views for the present workflow and a user may select one of these registered views, by, for example, touching the corresponding registered view. After completing act 209, the system may continue to act 211.

During act 211, the system may obtain view setting information (VSI) for the selected view. The VSI may include information related to each of the registered views. For example, the VSI may include information such as location and/or orientation of a view and/or of an ultrasound probe to obtain the view (e.g., to image the view) as well as parameters and/or settings (e.g., hereinafter both of which may be referred to as parameters for the sake of clarity) for the ultrasound probe for each view such as one or more of focus, depth, scan angle, etc. These parameters may be stored in association with each of the registered views. The VSI may be stored in a memory of the system. After completing act 211, the process may continue to act 213.

During act 213, the system may determine guidance information. The guidance information may be determined by the system and may provide guidance to move (e.g., linearly, non-linearly, and/or rotationally) the ultrasound probe from a current position to a position which corresponds with the selected view. Thus, for example, the system may determine difference information between a current position and/or orientation of the ultrasound probe and the desired position and/or orientation, respectively, of the ultrasound probe. The desired location and/or orientation of the ultrasound probe may be defined as a position and/or orientation which corresponds with that of the selected view. Thus, the guidance information may for example be based upon difference information (e.g., a difference between a desired position and/or orientation for a view and a current position and/or orientation of the ultrasound probe. However, any suitable method to determine the guidance information may be employed. After completing act 213, the system may continue to act 215.

During act 215, the system may output the determined guidance information. For example, in accordance with embodiments of the present system the system may form guidance instructions which may correspond with the determined guidance information and generate instructions, such as through use of a graphical user interface (GUI) including these guidance instructions in accordance with the determined guidance information. The system may then render this GUI on a rendering device of the system such as on a display, a speaker, etc. The guidance instructions may be based upon a rendering method employed by the system. For example, in accordance with some embodiments, the system may generate instructions such as move forward, reverse, turn right, turn left, etc., and/or graphic representations thereof, and display these instructions on a display of the system.

For example, in accordance with yet other embodiments, the system may render information related to the determined guidance information using any suitable guidance method such as lighting hard or soft keys, light-emitting-diodes (LEDs), driving a haptic device (e.g. provided on a handle of the ultrasound probe, etc.), etc. It is further envisioned that the system may determine an orientation of the user (e.g., the ultrasound clinician) and convert the guidance information accordingly so that the user may move the ultrasound probe to the desired position and/or orientation by manipulating controls of the ultrasound probe in accordance with guidance information rendered by the system.

It is also envisioned that the system may employ a robotic controller (e.g., a robotic actuator or the like) to robotically manipulate the ultrasound probe to a desired position and/or orientation. For example, the system may provide the guidance information to a robotic controller of the ultrasound probe which may then process the guidance information and provide corresponding information to one or more actuators of an ultrasound probe to effect a corresponding movement of the ultrasound probe. For example, the actuators may provide linear and/or rotational movement of the ultrasound probe such that the ultrasound probe may be moved to the determined position and/or orientation as set forth by the guidance information such that the ultrasound probe may be manipulated to a desired position and/or orientation which corresponds with a position and/or orientation of the selected area. After completing act 215, the system may continue to act 217.

During act 217, the system may determine whether the ultrasound probe is at, or is substantially at a position and/or orientation of the selected view (e.g., within a final threshold distance $\Delta_D$ and/or a final threshold orientation $\Delta_R$ of the selected view). Accordingly, in a case where it is determined that the ultrasound probe is at, or is substantially at (e.g., within a final threshold position $\Delta_D$ and/or a final threshold orientation $\Delta_R$) a location and/or orientation of the selected view, the process may continue to act 219. However, in a case where it is determined that the ultrasound probe is not at, or not substantially at (e.g., not within a final threshold position $\Delta_D$ and/or a final threshold orientation $\Delta_R$) a position and/or orientation of the selected view, the system may repeat act 213. To determine whether the ultrasound probe is at, or is substantially at a position and/or orientation of the selected view, the process may obtain information on a current position and/or orientation of the ultrasound probe, update the difference information and compare this updated difference information with the final threshold position $\Delta_D$ and/or a final threshold orientation $\Delta_R$, respectively. Accordingly, in a case where corresponding portions of the updated difference information are greater than the final threshold position $\Delta_D$ and/or the final threshold orientation $\Delta_R$, the system may determine that the ultrasound probe is not at, or not substantially at (e.g., not within a final threshold position $\Delta_D$ and/or a final threshold orientation $\Delta_R$) a position and/or orientation of the selected view. However, in a case where corresponding portions of the updated difference information are less than or equal to (e.g., not greater than) the final threshold position $\Delta_D$ and/or the final threshold orientation $\Delta_R$, the system may determine that the ultrasound probe is at, or substantially at (e.g., within a final threshold position $\Delta_D$ and/or a final threshold orientation $\Delta_R$) a position and/or orientation of the selected view and thereby, the system may continue to act 219.

During act 219, the system may indicate that the ultrasound probe is at a desired position (e.g., is at, or is substantially at a position and/or orientation) of the selected view. In other words, the ultrasound probe is positioned for the selected view. Accordingly, the system may render information indicating such on a rendering device of the system. For example, the system may highlight an overlay of the ultrasound probe using a green highlight to indicate to a clinician that it is in the desired position. The system may further provide information indicating such to one or more applications of the system such as to the robotic controller to stop motion and/or to lock the ultrasound probe in the current position and/or orientation (e.g., to prevent undesirable movement) and/or provide such information to an ultrasound image capture application which may use this information to begin an ultrasound image capture process as will be described below with respect to act 221. In yet other embodiments, the system may apply a brake and/or provide instructions to the clinician to apply a brake to prevent inadvertent movement of the ultrasound probe. After completing act 219, the system may continue to act 221.

During act 221, the system may capture ultrasound information at a location corresponding to the selected view and/or with the parameters corresponding to the selected view. This captured ultrasound information may then be processed to generate ultrasound image information suitable for rendering on a display of the system. After completing act 221, the system may continue to act 223.

During act 223, the system may store the captured ultrasound information in any suitable format (e.g., raw and/or processed) in a memory of the system in association with the selected view. Accordingly, the system may recall this ultrasound information at a later time in association with the selected view as desired. The ultrasound information may be stored as still and/or video image information in association with the parameters and/or in association with the corresponding selected view. Parameters including adjustments to parameters may be similarly stored in association with the corresponding selected view. In this way, historical information may be obtained including which views are accessed and/or adjusted. The historical information may be utilized to determine which views and/or parameters are used to produce a set of default views and corresponding parameters for a given workflow. For example, if for a given workflow, parameters are adjusted more than half the time from the parameters stored as a default, an average of the adjustments may be utilized for adjusting the parameters to a new default. Naturally views and/or parameters for a given patient related to one or more of the views may also be saved and recalled as desired. After completing act 223, the process may continue to act 225.

During act 225, the process may determine whether there are any other views in the current workflow to capture. Accordingly, in a case where it is determined that there is another view to capture, the process may repeat act 209 for the next view. However, in a case where it is determined that there are no other views to capture, the process may continue to act 227 where the process may end.

It is further envisioned that the system may store ultrasound image information, corresponding position, orientation and/or parameter information for the ultrasound probe in association with a view upon a request from a user. The system may then generate and render a menu indicating the views. The user may then select a view and the system may render the captured view and/or guidance information (from a current ultrasound location) to the desired view and/or parameter information related to the view as may be desired by the user and/or as may be set by the system (e.g., a default setting may determine what the system renders).

In accordance with embodiments of the present system, a user may toggle to select/deselect registered views. Moreover, a learning process may learn a procedure as it is performed by a user and this process may determine the views, parameters, etc.

Figure 4A:
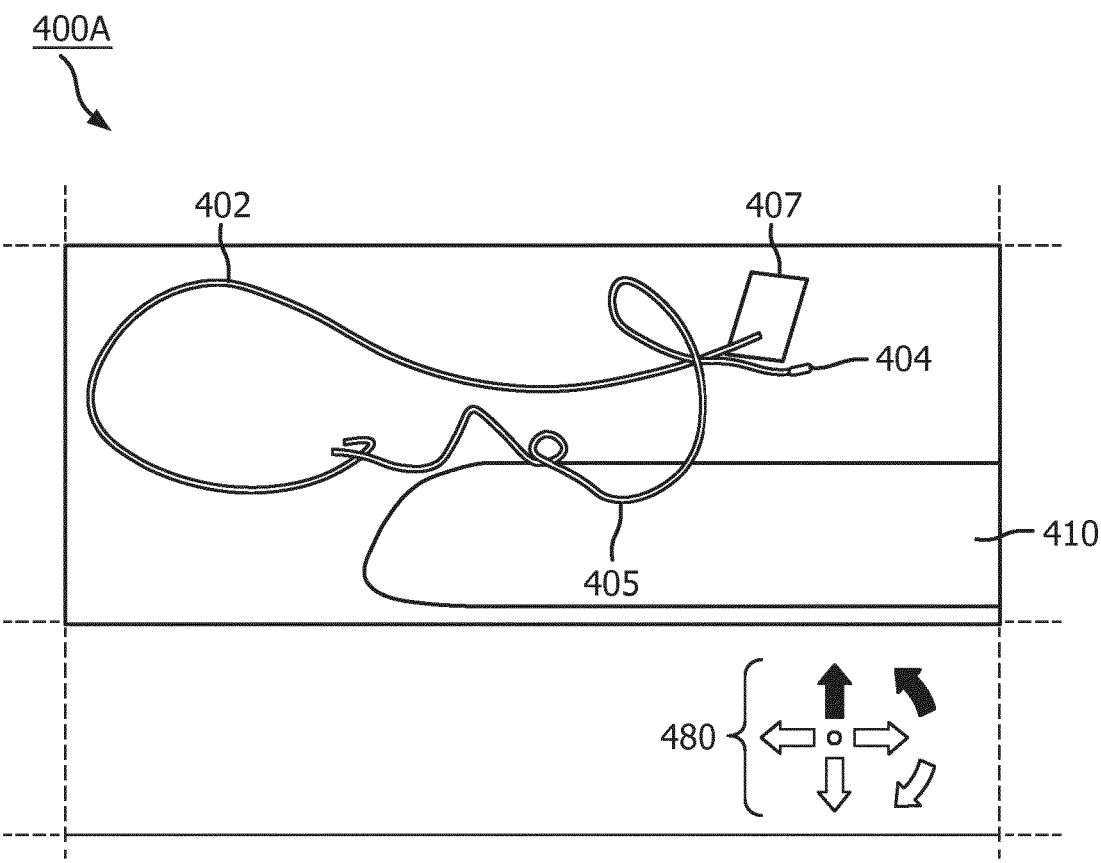
FIG. 4A shows a portion of a screenshot of an ultrasound probe navigated to an optimal first location corresponding with a first selected view in accordance with embodiments of the present system.
Figure 4B:
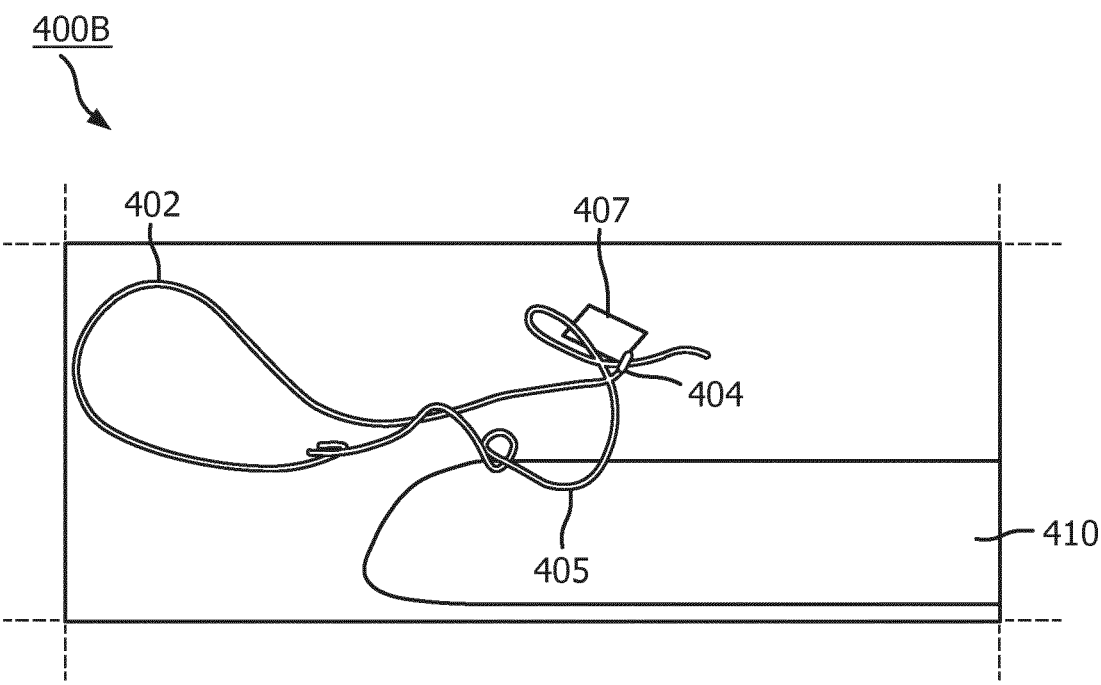
FIG. 4B shows a portion of a screenshot of the ultrasound probe of FIG. 3 navigated to an optimal second location corresponding with a second selected view in accordance with embodiments of the present system.

FIG. 4A shows a portion of a screenshot 400A, such as may be provided by a display, of an ultrasound probe 404 such as a FORS TEE situated at an end of a catheter 405. The ultrasound probe 404 may be positioned to capture a desired view such as an image volume 407 and may be navigated to an optimal first location corresponding with a first selected view in accordance with embodiments of the present system. The patient (not shown in the figure for clarity) may be positioned on a support structure 410, such as a surgical table. The system may determine a position of the ultrasound probe 404 using any suitable method such as by tracking a FORS SSD using a FORS tracking method or the like as described herein. Element 402 may represent a surgical instrument, such as a catheter, ablation instrument, etc. that is present in the view. Guidance messages such as arrows 480 may be rendered for guiding a user to control a location and/or orientation of the ultrasound probe 404 to a desired view location and/or orientation. The arrows 480 may be highlighted in solid to indicate a desired motion. Further, the arrows 480 may be highlighted using green for example when it is determined that the ultrasound probe 404 has reached a desired location. Further, in a case wherein more than one ultrasound probe is employed, guidance information for one or more (e.g., each) of the ultrasound probes may be determined and rendered in association with the corresponding ultrasound probe. FIG. 4B shows a portion of a screenshot 400B of the ultrasound probe 404 of FIG. 4A navigated to an optimal second location corresponding with a second selected view in accordance with embodiments of the present system. An SSD as described herein may be interrogated to determine the location of the ultrasound probe 404.

Figure 5:
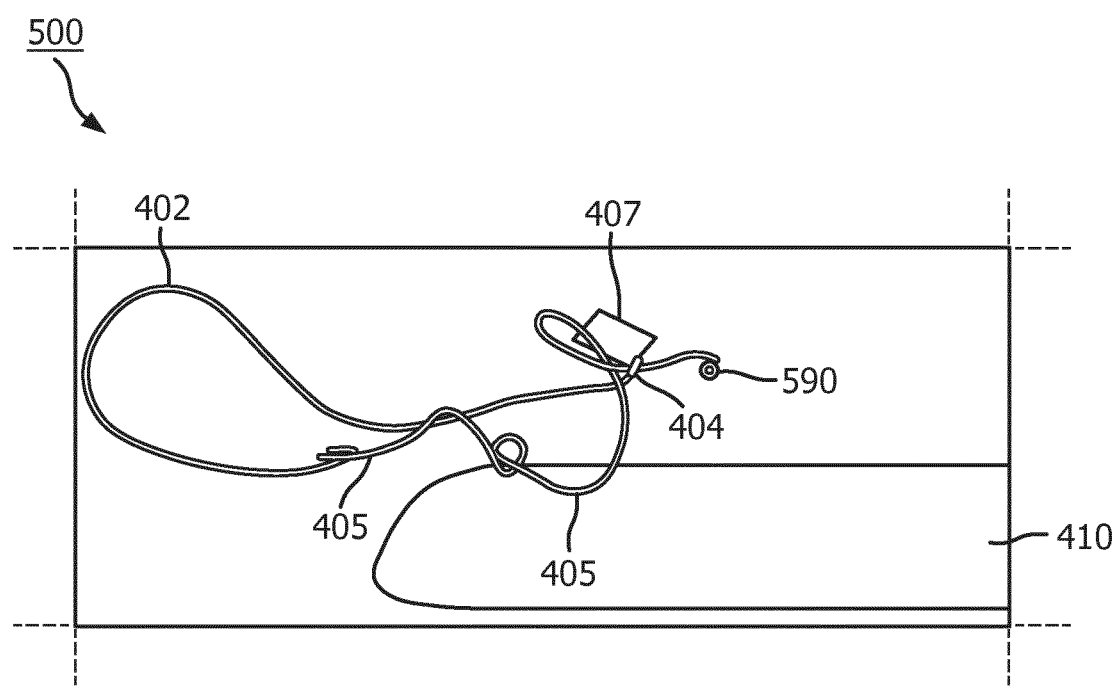
FIG. 5 shows a portion of a screenshot of the ultrasound probe of FIG. 4 navigated to the optimal second location corresponding with the second selected view and including an optional location indicator such as a circle in accordance with embodiments of the present system.

FIG. 5 shows a portion of a screenshot 500 of the ultrasound probe 404 of FIG. 4A navigated to the optimal second location corresponding with the second selected view and including an optional location indicator such as a circle 590 in accordance with embodiments of the present system. When the ultrasound probe 404 is determined to be at, or substantially at, the corresponding view (e.g., the second view in the current embodiments), the system may render an indicator such as the circle 590 indicating that the ultrasound probe 404 is at the corresponding location. However, in yet other embodiments, the circle 590 may include a highlight (e.g., green to indicate that the ultrasound probe 404 is at the proper location, red to indicate not at the proper location corresponding to the selected area, etc.). Further, the colors may also indicate the ultrasound parameter settings such as depth, focus etc. In yet other embodiments, it is envisioned that the system may generate arrows indicative of a direction and/or orientation to move the ultrasound probe to reach the desired area (location) of a corresponding view so as to capture the image volume 407. An SSD as described herein may be interrogated to determine the location of the ultrasound probe 404.

Figure 6:
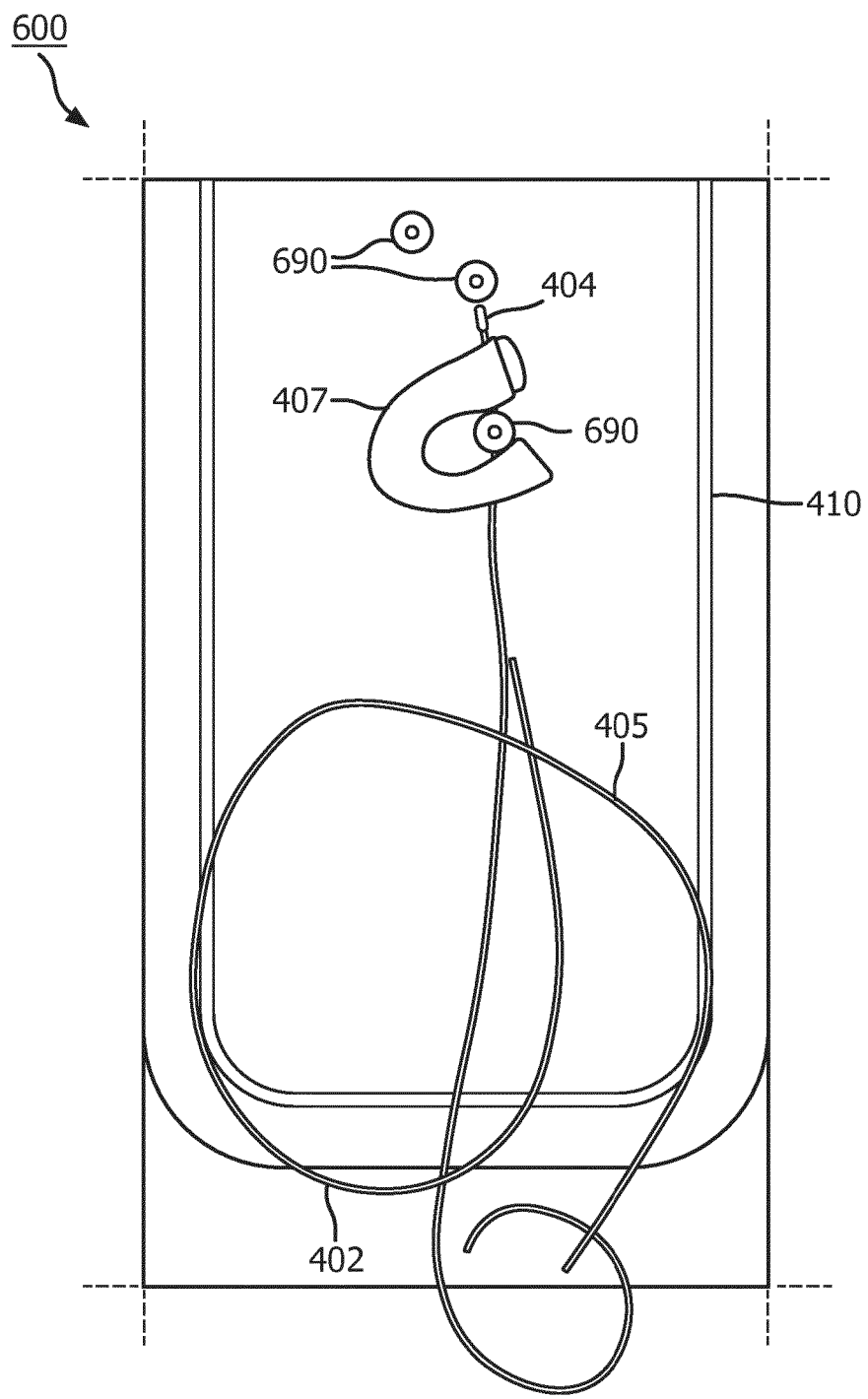
FIG. 6 shows a portion of a screenshot of the ultrasound probe navigated to an optimal location corresponding to a selected view and including optional location indicators such as circles in accordance with embodiments of the present system.

FIG. 6 shows a portion of a screenshot 600 of the ultrasound probe 404 navigated to an optimal location corresponding to a selected view and including optional location indicators such as circles 690 in accordance with embodiments of the present system. The circles 690 may indicate optimal locations for different views and may be colored or otherwise highlighted to indicate ultrasound parameter settings for each of these different views. For example, the colors may indicate the ultrasound parameter settings such as depth, focus etc. The different views may be either from a previously navigated position or built up from a model or database. An SSD may be interrogated to determine the location of the ultrasound probe 404 so that the ultrasound probe 404 may capture the corresponding view.

Accordingly, embodiments of the present system may provide a method in which FORS methods may be combined with ultrasound imaging to record and/or remember an ultrasound probe location and corresponding ultrasound parameter information for a location (e.g., a position and/or orientation of the ultrasonic probe) for a view. For example, a clinician such as an echocardiographer may navigate to a desired location and adjust the ultrasound parameters such as focus, depth, scan angle etc. The system may then store these settings in association with the desired location (e.g., a view) for later use. It is further envisioned that embodiments of the present system may provide a user an option to select any setting that is desired to be stored for later use in association with a selected view.

It is further envisioned that embodiments of the present system may automatically detect when an optimal position and/or view has been obtained based upon a comparison of optional positions and/or views stored in a memory of the system. When an optimal position is determined to be obtained, the system may inform a user of the same and may store settings and/or parameters used by an ultrasound probe to obtain ultrasound information of a corresponding view. It is further envisioned that a user may define how many positions and/or orientations (e.g., each corresponding to a view) are to be stored in a memory of the system depending on anatomy of a patient and/or a procedure being performed.

After the views and associated information are stored in a memory of the system, when a user (e.g., a clinician, a physician, etc.) desires to return to a previously-saved view (e.g., which may be considered a registered view), such as an LVOT, the system may provide a guidance function which may render appropriate guidance information (e.g., graphics such a arrows, etc., audio information (go right, etc.), haptic feedback, etc.) for a user to guide an ultrasound probe back to the previously saved view. In addition, ultrasound information (e.g., images) may then be captured for viewing using associated parameters that were previously stored in association with the corresponding saved view and/or may be recalled from a memory. It is further envisioned that a user may select a previously saved view, and the system may control a closed-loop robotic controller to automatically move an ultrasound probe to a desired position and set parameters, such as ultrasound parameters, in accordance with corresponding parameters so as to generate an optimal image.

It is also envisioned that embodiments of the present system may store optimal positions and corresponding ultrasound settings which may be used to generate optimal views for different procedures and different parts of these different procedures such as performing a transseptal puncture, navigating to the mitral valve, deploying a left atrial appendage (LAA) closure device, mitral clip, etc. During these procedures, the system may provide guidance so that workflow of a corresponding procedure may be simplified and shortened.

This may be especially so when performing procedures in difficult anatomies and/or when a good image may be difficult to obtain.

It is further envisioned that embodiments of the present system may support a combination of ultrasound probes (e.g., two or more ultrasound probes) including operating parameters, locations and/or orientations for each of these different ultrasound probes in a workflow of a procedure and automatically return to those different parameters, locations and/or orientations during different stages of the workflow. It is further envisioned that embodiments of the present system may support guidance to the locations and/or orientations of each of these different ultrasound probes in the workflow of a procedure and/or provide guidance to a robotic guidance system to automatically return the different ultrasound probes to corresponding locations and/or orientations, wherein one or more of the probes have a different location and/or orientation for one or more of the views. It is further envisioned that an alternate tracking modality such as electromagnetic tracking (EM), InSitu, optical tracking, etc., may be employed in addition to, or in conjunction with, FORS to act as a guidance system (e.g., GPS) and simplify navigation and re-navigation of one or more ultrasound probes during a workflow of a procedure.

Accordingly, embodiments of the present system may provide for a system and method in which finding and reclaiming salient views (e.g., standardized and/or personalized for the patient) of a surgical scene may performed. The system may provide intuitive instructions to a user so that the user may readily and easily place an ultrasound probe in a desired position and/or orientation to obtain ultrasound information at the desired position and/or orientation. The system may simplify visualization parameters and may remember these parameters such as ultrasound probe position, orientation, ultrasound image gain, depth, etc., and may set these parameters even across disjoint subsystems and/or probes. Accordingly, embodiments of the present system may employ OSS methods and the like to record and/or recall desired views in an ultrasound-guided procedure.

Examples of Ultrasound Related Portions of One or More Embodiments

As a clinician may attempt to navigate devices and effect therapy at a surgical site, the clinician may need to see the surrounding surgical site from multiple viewpoints in order to ensure proper care. For example, the clinician may need to adjust ultrasound settings and/or parameters such as gain, compression, contrast, depth, etc., for each view to obtain optimal image quality. Embodiments of the present system may incorporate the combination of ultrasound and OSS methods to assist the clinician in recording and recalling ultrasound settings, with the following variants: upon a user-initiated command (e.g., a button click), the system may read and store all relevant ultrasound settings (e.g., parameters), along with associated probe position(s) and/or orientation(s) as for example by OSS. In accordance with embodiments of the present system, these settings may then be recalled so that the clinician may restore a saved view at a later time. The system may further generate an overlay for example over a stored image of an area of interest, of a virtual ultrasound probe(s) indicating the proper position(s) and/or orientation(s) for one or more of the views.

Further, upon automatic detection of a salient view in an ultrasound image, embodiments of the present system may alert a clinician of this and may provide for example a user interface for the clinician to fine tune the probe position and/or orientation, as well as ultrasound settings and/or parameters as desired. Such an alert may be because the ultrasound image is registered to the patient anatomy, so a part of the anatomy that is in the view of the ultrasound is roughly known. This knowledge may be used in combination with image segmentation techniques which may be known in art and are not discussed further for the sake of clarity. One or more portions of operating parameters, locations, etc., may then be saved and subsequently recalled, as is discussed herein.

It is also envisioned that two or more recorded views (e.g., stored ultrasound images of multiple views, such as two, three, four, five views, . . . , up to all views for a given procedure) may be presented simultaneously to aid a clinician in evaluating a surgical scene, without the need to reposition the ultrasound probe or further adjust ultrasound settings and/or parameters. Since both the images and the ultrasound probe are registered to the patient anatomy (e.g., to the patient workspace), the images may be shown as separate views and/or provided together in a single image in a proper anatomical context (e.g., within a single image with the positioning based on the anatomical positioning provided by each view). Further, in cases where sequences of views are well established for a procedure, the system may assist and instruct the clinician on the steps to acquiring all desired views. These views may be stored as a library of views, or generated preoperatively by the clinician. These views may then be stored and form a part of a workflow for a procedure and may be recalled by the system and/or user when desired.

Examples of Procedure Related Portions of One or More Embodiments

A surgical procedure may entail acquisition of common anatomical viewpoints; the combination of OSS methods to track an ultrasound probe during a specific surgical procedure may be harnessed as follows. The system may determine whether ultrasound probe is at a desired view (e.g., at a proper position and/or orientation) using the OSS methods to track the ultrasound probe. Upon automatic detection of a desired ultrasound probe position and/or orientation (e.g., at a desired view), the system may alert a user (such as a clinician) of such and provide for the user to manually tune the ultrasound settings and/or parameters. Such an alert may be possible because the OSS methods may be registered to the patient anatomy, and because in many cases the desired views may be known a priori. The complete set of parameters and/or settings and the corresponding ultrasound information for each view may then be stored in a memory of the system as a view library of a process workflow and subsequently recalled during the process workflow as discussed herein. It is further envisioned that in embodiments of the present system, stored desired standard views for a process workflow may be displayed as an augmented reality visual rendering, indicating to the user all of the views to be collected for proper evaluation of the surgical scene (e.g., with the views put together into a single image or otherwise positioned in proper anatomical positions) during a future process workflow. In accordance with embodiments, the views may be presented in an order following the procedure work flow and/or may be ordered/re-ordered as desired.

Examples of Shape-Sensing Related Portions of One or More Embodiments

In accordance with one or more embodiments, a virtual overlay of the probe may be rendered to indicate to the user (e.g., a clinician, etc.) where the ultrasound probe should be placed in order to acquire the views desired/needed to perform a surgical procedure. For example, the shape of one or more contiguous portions of the ultrasound probe (e.g., up to all of the probe or inserted portion) may be rendered, thus, providing to the user richer information on how the ultrasound probe should be positioned and/or oriented to acquire a desired view or views.

Full shape information (such as of an inserted portion) may be rendered and may be particularly useful when manual guidance of an ultrasound probe is used. Unlike a robotic manipulator which may readily manipulate an ultrasound probe to a desired position and/or orientation, a human operator (e.g., a clinician, etc.) may find the same task challenging due to the unintuitive hand-eye coordination caused by having to cognitively map disjoint coordinate systems. Accordingly, full shape information rendering of the ultrasound probe, which may be otherwise redundant, provides information (e.g., using a graphics display, etc.) to the human operator about the context of the probe position and/or orientation. Furthermore, since the probe may be tracked using OSS methods, the image or probe coordinate system may be registered to the user's point-of-view, thus unifying the disjoint coordinate system and simplifying manual guidance of the ultrasound probe during a process workflow. In a robotic procedure, a user may finalize a position and/or orientation obtained by the robotic procedure to adjust the position to a final position and/or orientation as desired.

Figure 7:
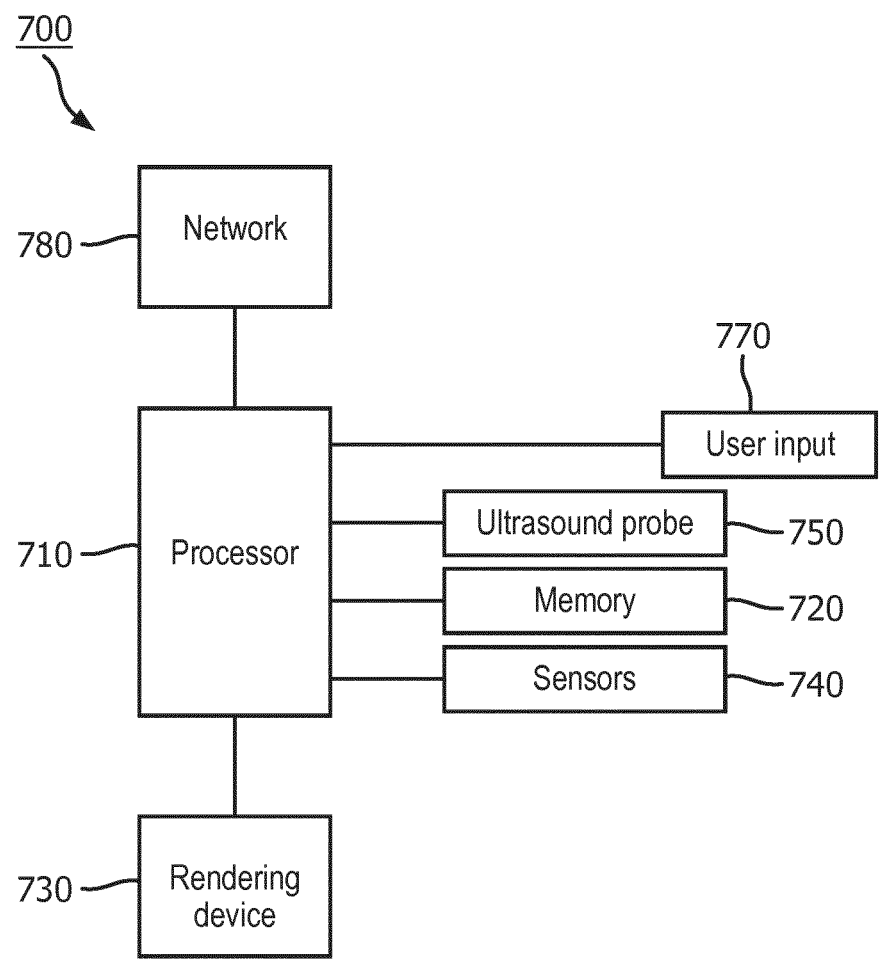
FIG. 7 shows a portion of a system in accordance with embodiments of the present system.

FIG. 7 shows a portion of a system 700 in accordance with embodiments of the present system. For example, a portion of the present system may include a processor 710 (e.g., a controller) operationally coupled to a memory 720, a user interface (UI) including a rendering device such as a display 730, sensors 740 such as a shape sensing device (SSD), one or more ultrasound probes 750, and a user input device 770. The memory 720 may be any type of device for storing application data as well as other data related to the described operation. The application data and other data are received by the processor 710 for configuring (e.g., programming) the processor 710 to perform operation acts in accordance with the present system. The processor 710 so configured becomes a special purpose machine particularly suited for performing in accordance with embodiments of the present system. The operation acts may include configuring a system by, for example, a registration system in accordance with system settings. The operation acts may also include the processor 710 obtaining a workflow from the memory 720 including desired views and associated parameters, such as parameters related to settings for the one or more ultrasound probes 750 and the sensors 740 including correlation information that correlates a positon of the sensors 740 in relation to the ultrasound probe 750 (e.g., provides offset information relating a position of the sensors 740 to the position of the ultrasound probe (750)).

The processor 710 may control one or more tracking systems (e.g., the sensors 740) such as utilizing a FORS tracking method so that sensor information signals indicative of a location of the sensors 740 may be generated. The processor 710 may process received signals such as sensor information, transform these signals to location signals, and may generate content which may include image information (e.g., still and/or video images including ultrasound image information), data, parameters, positions, orientations, guidance information and/or graphs that may be rendered on, for example, a UI of the system such as on the display 730, a speaker, etc. The content may include image information as may be generated by a medical imaging system of the present system, guidance information, etc. Further, the content may then be stored in a memory of the system such as the memory 720 for later use. Thus, operation acts may include requesting, providing, and/or rendering of the content. The processor 710 may render the content such as video information on a UI of the system such as a display of the system. The processor 710 may determine and render the UI of the system such as on the display of the system.

The user input device 770 may include a keyboard, a mouse, a trackball, or other device, such as a touch-sensitive display, which may be stand alone or part of a system, such as part of a personal computer, a personal digital assistant (PDA), a mobile phone (e.g., a smart phone), a monitor, a smart or dumb terminal or other device for communicating with the processor 710 via any operable link such as a wired and/or wireless communication link. The user input device 770 may be operable for interacting with the processor 710 including enabling interaction within a UI as described herein. Clearly the processor 710, the memory 720, display 730, and/or user input device 770 may all or partly be a portion of a computer system or other device such as a client and/or server.

The methods of the present system are particularly suited to be carried out by a computer software program, such program containing modules corresponding to one or more of the individual steps, acts, modules, etc., described and/or envisioned by the present system. Such program may of course be embodied in a computer-readable medium, such as an integrated chip, a peripheral device or memory, such as the memory 720 or other memory coupled to the processor 710.

The program and/or program portions contained in the memory 720 may configure the processor 710 to implement the methods, operational acts, and functions disclosed herein. The memories may be distributed, for example between the clients and/or servers, or local, and the processor 710, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 710. With this definition, information accessible through a network is still within the memory, for instance, because the processor 710 may retrieve the information from the network for operation in accordance with the present system.

The processor 710 is operable for providing control signals and/or performing operations in response to input signals from the user input device 770 as well as in response to other devices of a network and executing instructions stored in the memory 720. The processor 710 may include one or more of a microprocessor, an application-specific or general-use integrated circuit(s), a logic device, etc. Further, the processor 710 may be a dedicated processor for performing in accordance with the present system or may be a particularly programmed general-purpose processor wherein only one of many functions operates for performing in accordance with the present system. The processor 710 may operate utilizing a program portion, multiple program segments, and/or may be a hardware device utilizing a dedicated or multi-purpose integrated circuit. Embodiments of the present system may provide imaging methods to acquire and/or reconstruct images. Suitable applications may include imaging systems such as ultrasound images.

However, without limitation it should be understood that embodiments of the present system may further include imaging systems such as MRI, (computer-aided tomography (CAT), optical, X-ray, and/or combinations thereof. Further, embodiments of the present system may be ideally suited for surgical interventional techniques which may generate and render image and/or sensor information from one or more imaging systems (e.g., ultrasound, CT scans, MRI, etc.) having different coordinate systems wherein results are provided (e.g., images, position and/or orientation information) in real-time with a unified coordinate system.

Further variations of the present system would readily occur to a person of ordinary skill in the art and are encompassed by the following claims. Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise;

h) no specific sequence of acts or steps is intended to be required unless specifically indicated;

i) the term "plurality of" an element includes two or more of the claimed element, and does not imply any particular range of number of elements; that is, a plurality of elements may be as few as two elements, and may include an immeasurable number of elements; and j) the term and/or and formatives thereof should be understood to mean that only one or more of the listed elements may need to be suitably present in the system in accordance with the claims recitation and in accordance with one or more embodiments of the present system.

What is claimed is:

1. A surgical guidance system, comprising:
    a memory;
    a rendering device;
    an ultrasound probe;
    a shape-sensing-device (SSD) associated with the ultrasound probe and having a predetermined position and orientation with regard to the ultrasound probe; and
    a controller coupled to the memory, the rendering device and the SSD, the controller being configured to:
    determine at least one of a location and an orientation of the ultrasound probe based upon position sensor information (PSI) received from the SSD,
    select a view of a plurality of views of a workflow that are stored in the memory;
    select a procedure type from a workflow table stored in the memory,
    obtain view setting information (VSI) for the selected view from the memory, the VSI comprising parameters and at least one of a position and an orientation of the ultrasound probe for each of the plurality of views,
    determine guidance information based upon a comparison of the determined at least one of the location and the orientation of the ultrasound probe and the at least one of a position and orientation of the ultrasound probe for the selected view, and
    render the determined guidance information on the rendering device and set ultrasound probe parameters based on the parameters of the VSI for the selected view.

2. The surgical guidance system of claim 1, wherein the SSD comprises at least one position sensor and the controller is further configured to query the at least one position sensor to obtain the PSI, the PSI being indicative of at least one of a position and orientation of the at least one position sensor relative to a workspace.

3. The surgical guidance system of claim 1, wherein the controller is further configured to render the determined guidance information as directional indications to guide the ultrasound probe to at least one of a position and orientation of the ultrasound probe for the selected view.

4. The surgical guidance system of claim 1, wherein the controller is further configured to display simultaneously on the rendering device two or more of the plurality of views of the workflow.

5. The surgical guidance system of claim 4, wherein the controller is further configured to display on the rendering device an indication for each of the two or more of the plurality of views.

6. The surgical guidance system of claim 4, wherein the controller is further configured to display on the rendering device the two or more of the plurality of views as a single view with the two or more of the plurality of views anatomically positioned.

7. The surgical guidance system of claim 1, wherein the controller is coupled to at least one transducer of the ultrasound probe to obtain ultrasound image information using the set ultrasound probe parameters.

8. The surgical guidance system of claim 7, wherein the controller is further configured to reconstruct an image based upon the ultrasound image information in accordance with the set ultrasound probe parameters.

9. The surgical guidance system of claim 1, wherein the controller is further configured to associate and store two or more of current parameters, location, orientation, and ultrasound information of the ultrasound probe in association with the selected view.

10. The surgical guidance system of claim 1, wherein the controller is further configured to determine which of the plurality of views is closest to the determined at least one of location and orientation of the ultrasound probe and select the view based on which view is determined closest.

11. The surgical guidance system of claim 1, wherein the controller is further configured to use landmarks to guide the ultrasound probe.

12. The surgical guidance system of claim 1, wherein the controller is further configured to select the view based on a threshold.

13. A method for guiding an ultrasound probe for obtaining ultrasound information, the method comprising:
- determining at least one of location and orientation of the ultrasound probe based upon position sensor information (PSI);
- selecting a view of a plurality of views of a workflow that are stored in a memory;
- selecting a procedure type from a workflow table stored in the memory,
- obtaining view setting information (VSI) for the selected view, the VSI comprising information related to parameters and at least one of a position an orientation of the ultrasound probe for each of the views;
- determining guidance information based upon a comparison of the at least one of the location and the orientation of the ultrasound probe and the at least one of a position and orientation of the ultrasound probe for the selected view; and
- outputting the determined guidance information and setting ultrasound probe parameters based on the parameters of the VSI for the selected view.

14. The method of claim 13, wherein the method further comprises an act of querying at least one position sensor of a shape-sensing-device (SSD) to obtain the PSI, the PSI being indicative of at least one of a position and orientation of the at least one position sensor relative to a workspace.

15. The method of claim 13, wherein the outputting of the determined guidance information comprises acts of generating guidance instructions corresponding to the determined guidance information and rendering the generated guidance instructions on a rendering device.

16. The method of claim 13, wherein the outputting comprises outputting the determined guidance information as directional indications to guide the ultrasound probe to at least one of a position and orientation of the ultrasound probe for the selected view.

17. The method of claim 13, further comprising using landmarks to guide the ultrasound probe.

18. The method of claim 13, further comprising selecting the view based on a threshold.

19. A non-transitory computer readable medium comprising computer instructions which, when executed by a processor, configure the processor to:
- determine at least one of location and orientation of an ultrasound probe based upon position sensor information (PSI);
- select a view of at least one registered view of a workflow;
- select a procedure type from a workflow table stored in the memory,
- obtain view setting information (VSI) for the selected view, the VSI comprising information related to parameters for each of the registered views and at least one of a position and orientation of the ultrasound probe for each of the views;
- determine guidance information based upon a comparison of the at least one of the location and the orientation of the ultrasound probe and the at least one of a position and orientation of the ultrasound probe for the selected view; and
- output the determined guidance information and setting ultrasound probe parameters based on the parameters of the VSI for the selected view.

20. The non-transitory computer readable medium of claim 19, wherein the instructions, when executed by the processor, further cause the processor to query at least one position sensor of a shape-sensing-device (SSD) to obtain the PSI, the PSI being indicative of at least one of a position and orientation of the at least one position sensor relative to a workspace.

21. The non-transitory computer readable medium of claim 19, wherein the instructions, when executed by the processor, further cause the processor to display simultaneously two or more of the plurality of views of the workflow.

22. The non-transitory computer readable medium of claim 21, wherein the instructions, when executed by the processor, further cause the processor to display simultaneously the two or more of the plurality of views as a single view with the two or more of the plurality of views anatomically positioned.

23. The non-transitory computer readable medium of claim 21, wherein the instructions, when executed by the processor further cause the processor to generate guidance instructions corresponding to the determined guidance information and render the generated guidance instructions on a rendering device.

24. The non-transitory computer readable medium of claim 21, wherein the instructions, when executed by the processor further cause the processor to output the determined guidance information as directional indications to guide the ultrasound probe to at least one of a position and orientation of the ultrasound probe for the selected view.

25. The non-transitory computer readable medium of claim 19, wherein the instructions, when executed by the processor, further cause the processor to use landmarks to guide the ultrasound probe.

26. The non-transitory computer readable medium of claim 19, wherein the instructions, when executed by the processor, further cause the processor to select the view based on a threshold.

* * * * *